United States Patent [19]

Noble et al.

[11] Patent Number: 5,484,611
[45] Date of Patent: Jan. 16, 1996

[54] METHOD OF PRODUCING A FATTY ACID

[75] Inventors: Raymond C. Noble, Ayr, Scotland; Massimo Cocchi, Bologna, Italy

[73] Assignee: The Scottish Agricultural College, Ayr, Scotland

[21] Appl. No.: 106,297

[22] Filed: Aug. 13, 1993

Related U.S. Application Data

[63] Continuation-in-part of Ser. No. 914,114, Jul. 15, 1992, abandoned.

[51] Int. Cl.$^6$ ................................................ A61K 35/12
[52] U.S. Cl. .................... 424/570; 424/451; 424/464; 424/502; 424/522; 514/558; 514/560; 554/175
[58] Field of Search ................ 554/21, 175; 514/558, 514/560; 424/451, 464, 489, 502, 522, 570

[56] References Cited

U.S. PATENT DOCUMENTS

| | | | |
|---|---|---|---|
| 5,084,215 | 1/1992 | Kearns et al. | 260/403 |
| 5,112,956 | 5/1992 | Tang et al. | 530/424 |
| 5,130,061 | 7/1992 | Cornieri et al. | |

FOREIGN PATENT DOCUMENTS

| | | |
|---|---|---|
| 0342795 | 4/1989 | European Pat. Off. . |
| 0342795 | 11/1989 | European Pat. Off. . |
| 2599382 | 12/1987 | France . |
| 3296665 | 2/1988 | Japan . |
| 0164852 | 7/1988 | Japan . |
| 3020397 | 1/1991 | Japan . |
| 89/05655 | 6/1989 | WIPO . |

OTHER PUBLICATIONS

Ansari, Khurshed; Neurochem. Res., 15(1) 7–11, 1990.
Noble; Med. Sci. Res.; 1989; No. 17, 251–252.
R.A.G.G. Times, No. 5, Mar. 1992, document of the Nutrition Society Reproduction and Growth Group.
Memorandum and Articles of Association of the Nutrition Scociety, Aug. 1990.
Nutrition Society membership application, no date, believed to be prior to Mar. 1992.
R. C. Noble, et al., Polyunsaturated fatty acid levels in the phosphyglycerides of chick embryo tissues and a response to light stimulus, Med. Sci, Res., 1989, pp. 251–252.
R. C. Noble, et al., The relationship between the supply and demand for essential polyunsaturated fatty acids during mammalian and avian embryonic development, Research & Development in Agriculture, 6.2 (1989) pp. 65–69.
World Patent Index Latest "Section ch week 8933" 1989, Derwent Publications Ltd. class D. AN 89–307256 and SE–A–8705122 (Abstract).
Jordi Folch, et al., A simple Method for the Isolation and Purification of Total Lipides from Animal Tissues, The Journal of Biological Chemistry, vol. 226, No. 1, 1957, pp. 497–509.
Arachidonic and Docosahexanoic Acid Content of Bovine Brain Myelin: Implications for the Pathogenesis of Multiple Sclerosis, Krushed A. Ansari et al., Neurochemical Research, vol. 15, No. 1, 1990, pp. 7–11.
R. C. Noble et al., Unsaturated Fatty Acid Compositional Changes and Desaturation During the Embryonic Development of the Chicken (Gallus domesticus) Lipids, vol. 20, No. 5, 1985, pp. 278–282.

Primary Examiner—José G. Dees
Assistant Examiner—Samuel Barts
Attorney, Agent, or Firm—Ratner & Prestia

[57] ABSTRACT

A method of producing docosahexaenoic acid and a method of treatment of animal bodies by administering the docosahexaenoic acid, the docosahexaenoic acid being linked to phospholipids which have been selectively purified from the brains of preferably 1–3 day old chicks.

11 Claims, No Drawings

METHOD OF PRODUCING A FATTY ACID

This is a continuation in part of our earlier application Ser. No. 07/914,114. Filed Jul. 15, 1992, now abandoned.

This invention relates to a method of producing a fatty acid in treating the body.

Fatty acids play an important role in the functioning of human and animal bodies, and the particular fatty acid with which this invention is concerned, namely docosahexaenoic acid (DHA), is known to have beneficial effect on at least the retina, gonads and brain. It is also known that the levels of this fatty acid reduce with age, and it is therefore desirable to supplement these levels by introduction from other sources.

Fish oil, for example, contains significant amounts of DHA but does not contain a compatible solubilizing agent which is necessary for the incorporation of the DHA into the tissues of the body; DHA from this source is not therefore a practical proposition.

Bovine brain is also known to contain DHA. Christie ("The composition, structure and function of lipids in the tissues of ruminant animals" in "lipid metabolism in ruminant animals" 1981) discloses that 6.6% of the percentage weight of bovine brain phosphatidyl ethanolamine fraction is comprised of DHA, and that the phosphatidyl serine and phosphatidyl inositol fractions contain 2.6% and 2.4% DHA respectively.

Ansari and Shoeman (Neurochemical Research Vol 15 No. 1) teach that DHA and arachidonic acid are present in bovine brain myelin, although the amounts of DHA which are recoverable from this source are very low.

It is also known from Noble (Medical Science Research 1989 No 17, pages 251–252) that DHA is present in the brains of chick embryos before they are hatched. Noble does not give any indication as to the relative amounts of DHA present in the various phospholipids in the embryonic chick brain, nor does Noble disclose how the DHA might be used in a method of treatment.

According to the present invention there is provided a method of producing docosahexaenoic acid comprising extracting from the brains of hatched chickens, a mixture of docosahexaenoic acid-linked phospholipids, purifying from the mixture of docosahexaenoic acid-linked phospholipids the fractions of phosphatidyl ethanolamine, phosphatidyl serine, and phosphatidyl inositol, and combining said fractions together.

It has been found that the resulting combination of the fractions of docosahexaenoic acid-linked phospholipid finds its way naturally to the target organs which require enhancement of DHA; in the absence of the phospholipid this does not happen and DHA solubilised with other materials such as emulsifiers is not taken up by the target organs.

The combined fractions of docosahexaenoic acid-linked phospholipid can then be introduced for example orally, intravenously or parenterally into an animal body to be treated and it will target areas of the body such as the retina, the gonads and the brain. It will be appreciated by the reader that the term "animal" as used in this Specification and Claims also includes humans.

The presence of the phospholipids phosphatidyl ethanolamine, phosphatidyl serine, and phosphatidyl inositol are themselves beneficial as well as acting to guide the DHA to the desired areas. A further advantage is that DHA in combination with phospholipid is solubilised and is therefore easily received into the body.

Further according to the present invention there is provided a method of treatment of an animal body, comprising administering to the body docosahexaenoic acid in biocompatible form which has been produced by extracting from the brains of hatched chickens, a mixture of docosahexaenoic acid-linked phospholipids, purifying from the mixture of docosahexaenoic acid-linked phospholipids the fractions of phosphatidyl ethanolamine, phosphatidyl serine, and phosphatidyl inositol, and combining said fractions together.

Preferably the DHA is extracted from chicks up to three days after hatching, preferably up to two days after hatching, and most preferably within one day of hatching.

The levels of DHA in young and embryonic chicken brains are remarkable and surprisingly high, being of the order of up to 13% of the total fatty acid content. The inventors have made the further surprising discovery that the level of DHA in a mixture of the selected phospholipids phosphatidyl ethanolamine, phosphatidyl serine, and phosphatidyl inositol is increased as compared to the total phospholipid, thereby further enhancing the yield of DHA.

The commercial feasibility is enhanced by the fact that the majority of chicks are hatched in controlled environments producing many millions of chicks daily, and approximately one-half of these, the male chicks, are currently of no commercial use and are killed early in life for no return. The present invention therefore provides a substantial means of obtaining an economic benefit from these male chicks. It has been calculated that from the 40,000,000 male chicks which are killed in the UK alone each year, a yield of 400 Kg of surprisingly DHA-rich phospholipid can be obtained.

As the chick embryos hatch and grow to maturity the level of DHA in their brains diminishes, and the most commercially viable time to extract the DHA is shortly after hatching; this again adds to the economic benefits of the invention as it is not necessary to maintain the life of male chicks beyond the first few days. The value of female chicks in later life outweighs the benefit to be derived from killing them before hatching for the extraction of DHA. Thus the risk of killing a female chick embryo makes it commercially unviable to extract the DHA from the brains of unhatched chick embryos since it is not possible to determine the sex of the embryo before hatching.

The DHA-linked phospholipid from chicken brains and each single phospholipid fraction of the same source is conveniently in a form suitable for oral, intravenous or parental administration in a suitable pharmaceutical or dietetic vehicle, for example tablets, capsules, powder preparation, and lyophilized preparations to be diluted in appropriate solvents or in phials.

Advantageously a preservative may be incorporated in the preparation. Antioxidant (natural or synthetic) agents have been found suitable for the purpose.

An embodiment of the present invention will now be described by way of illustration in the following example.

EXAMPLE

1. Sample: Complete brain from day old male chicks.
2. Total lipid extraction: the whole brain tissue was homogenized and refluxed in 2:1 (v/v) chloroform::methanol, the non-lipid contaminants were removed by filtration and subsequent washing of the eluant with 0.88 per cent (w/v) potassium chloride and a lipid-rich chloroform phase was obtained by centrifugation at low speed.
3. Phospholipid preparation and analysis: the total lipids were fractionated into the major lipid classes on thin layer chromatoplates of silica gel G, thickness 0.25 mm, using a solvent system of hexane: di-ethyl ether: formic acid (80:20:1 v/v/v). Following visualization under ultraviolet light after spraying with 0.1 per cent w/v solution of 2,7-dichlorofluorescein in methanol, the phospholipid was eluted from the silica gel by washing with 3×5 ml of chloroform: methanol: water (5:5:1 v/v/v). The phospholipid was transmethylated by refluxing with methanol: toluene: sulphuric acid (20:10:1 v/v/v). Gas liquid chromatography of the methyl fatty acid ester derivatives on a packed column of 15 per cent CP Sil 84 on Chromosorb WHP enabled the quantification of the relative proportions of the major long chain fatty acids present.
4. Fatty acid composition: the proportion (per cent) by weight of the major fatty acids in total phospholipid was—palmitic 35.9, palmitoleic acid <1, stearic acid 16.2, oleic acid 16.4, linoleic acid 2.2, linolenic acid <1, arachidonic acid 9.6, docosahexaenoic acid 17.7.

The total phospholipid mixture was then applied to thin layer chromatoplates of silica gel D (0.5 mm) and separated into its major phospholipid fractions by chromatography using a solvent of chloroform: methanol: acetic acid: water in a ratio of 50:30:8:4 (v/v/v/v). Following visualization under u.v. light as described in 3 above, the separated fractions of phosphatidyl ethanolamine, phosphatidyl serine, and phosphatidyl inositol (in combination amounting to approximately 56% of the total phospholipid) were eluted from the silica gel by washing with 3×5 ml of chloroform: methanol: water in a ratio of 5:5:1 (v/v/v). The fatty acids of the fractions separately and in combination were determined by gas liquid chromatography as described in 3 above and further examples of these results are shown in Table 1 below.

TABLE 1

| Major Polyunsaturated % of total fatty acids | Total Phospholipid | Phosphatidyl ethanolamine + serine + inositol |
|---|---|---|
| 18:2 (n-6) Linoleic | 1.1 | 1.3 |
| 18:3 (n-3) Linolenic | <1.0 | <1.0 |
| 18:4 (n-3) Stearodonic | <1.0 | <1.0 |
| 20:3 (n-6) Icosotrienoic | <1.0 | <1.0 |
| 20:4 (n-6) Arachidonic | 10.8 | 13.8 |
| 22:6 (n-3) Docosahexaenoic | 13.3 | 29.2 |
| % Phospholipid in total lipid | 60% | |
| % of total Phospholipid | | 56% |

As can be clearly seen from the above table, the levels of DHA are increased in the pooled fractions of phosphatidyl ethanolamine, phosphatidyl serine and phosphatidyl inositol as compared with the total phospholipid.

The DHA in combination with the selected phospholipids obtained by this method was then tested as follows:

Sixteen rats, all 18 months old, were divided into two groups of eight. To one group the DHA-phospholipid sonicated in a physiological medium was administered by intraperitoneal injection at a dosage of 50 mg DHA-phospholipid each day for 7 days; 25% by weight of the DHA-phospholipid consisted of DHA.

The other group of rats received injections of the same amount of physiological medium as the test group, but without the DHA-phospholipid.

After one week the rats' blood was sampled by heart puncture and the rats were killed by decapitation. Tissue was taken for analysis and plasma was obtained by centrifugation of the blood.

Results showed that triglyceride levels were 115 mg per 100 ml in the test group and 315 mg per 100 ml in the control group, representing a reduction of 63% in the test group. A marked reduction was also observed in the Holman Index (triene/tetraene fatty acid ratio) in the test group.

The fatty acid profile of the brain, gonads and retina showed significant improvement in the DHA content in the test group as compared to the controls.

Diseases and disorders for which the DHA-phospholipid obtained in the present invention is effective are, for example:

1. Degenerative diseases of retina caused by aging;
2. Degenerative diseases of brain and nervous system caused by aging;
3. Degenerative diseases of gonads caused by aging and male infertility;
4. Nutritional care for the critically ill;
5. Organ failure induced by metabolic stress of cell membrane;
6. Acute inflammatory response;
7. Viral infection;
8. Diabetic retinopathy;
9. Hypertriglyceridemia;
10. Other conditions which reduce the DHA synthesis from its precursor by the blockage of Delta 6, Delta 5, Delta 4 Desaturase enzyme.

This invention is also the use of combined DHA-phospholipid obtained from chicken brains in the treatment of organs in animal bodies.

Modifications and improvements may be incorporated without departing from the scope of the invention.

We claim:

1. A method of producing docosahexaenoic acid linked with phospholipid, the method comprising extracting from the brains of hatched chickens, a mixture of docosahexaenoic acid-linked phospholipids, purifying from said mixture of docosahexaenoic acid-linked phospholipids the fractions of phosphatidyl choline, phosphatidyl serine and phosphatidyl inositol, and combining said fractions together.

2. A method according claim 1, wherein the extraction is performed using chicks up to 3 days after hatching.

3. A method according to claim 1, wherein the extraction is performed using chicks within 1 day of hatching.

4. A method according to claim 1, wherein the chicken brains are male chicken brains.

5. A method according to claim 1, wherein after extraction the docosahexaenoic acid linked with the phospholipid is made into a form suitable for oral, intravenous or parenteral administration.

6. A method according to claim 5, wherein the docosahexaenoic acid linked with the phospholipid is made into the form of tablets, capsules, powder or solution.

7. A method according to claim 5, wherein a preservative is included in said form suitable for oral or parenteral administration.

8. A method according to claim 1, wherein the extraction is performed by homogenising the brain tissue, removing non-lipid components, fractionating into major lipid classes and eluting the docosahexaenoic acid linked with the phospholipid.

9. A method of treatment of an animal body, comprising administering to the body a composition in biocompatible form which contains docosahexaenoic acid-linked phospholipids wherein said phospholipids are phosphatidyl ethanolamine, phosphatidyl serine and phosphatidyl inositol, said docosahexaenoic acid-linked phospholipids having been extracted from the brain of a hatched chicken.

10. A method according to claim 1, wherein said combined pool also contains arachidonic acid.

11. A method according to claim 10, wherein the ratio of docosahexaenoic acid to arachidonic acid is approximately 2:1.

* * * * *